United States Patent

Ebel et al.

Patent Number: 5,362,875
Date of Patent: Nov. 8, 1994

[54] PREPARATION OF PYRIMIDINES

[75] Inventors: Klaus Ebel, Ludwigshafen; Juergen Schroeder, Viernheim, both of Germany

[73] Assignee: BASF Aktiengesellschaft, Ludwigshafen, Germany

[21] Appl. No.: 75,041

[22] Filed: Jun. 10, 1993

[30] Foreign Application Priority Data

Jun. 17, 1992 [DE] Germany .................. 4219789

[51] Int. Cl.$^5$ ........................... C07D 239/26
[52] U.S. Cl. ................................. 544/242
[58] Field of Search ....................... 544/242

[56] References Cited

FOREIGN PATENT DOCUMENTS

| | | |
|---|---|---|
| 192299 | 8/1986 | European Pat. Off. . |
| 4024259 | 2/1992 | Germany . |
| 2/104577 | 10/1988 | Japan . |
| 211577 | 1/1990 | Japan . |
| 2104557 | 4/1990 | Japan . |

OTHER PUBLICATIONS

Pews, *Heterocycles*, vol. 27 (1988) pp. 1867–1871.

Primary Examiner—John M. Ford
Attorney, Agent, or Firm—John H. Shurtleff

[57] ABSTRACT

A process for preparing pyrimidines of the formula I

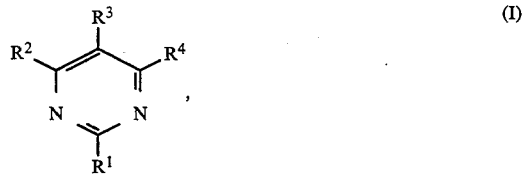

(I)

where
$R^1$ is $C_1$–$C_8$-alkyl, $C_7$–$C_{12}$-aralkyl or phenyl and
$R^2$, $R^3$ and $R^4$ are each, independently of one another, hydrogen, $C_1$–$C_8$-alkyl, $C_7$–$C_{12}$-aralkyl or phenyl, entails reacting nitriles of the formula II $$R^1-C\equiv N \qquad (II)$$

where $R^1$ has the abovementioned meaning, with 1,3-diaminopropanes of the formula III

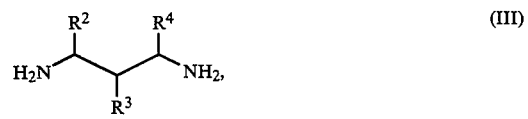

(III)

where $R^2$ to $R^4$ have the abovementioned meanings, in the presence of copper(II) acetate at from 150° to 250° C. to give the tetrahydropyrimidine of the formula IV

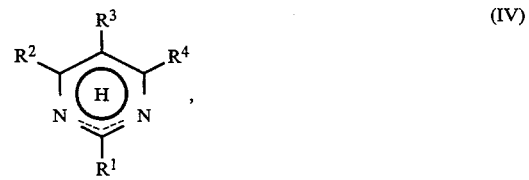

(IV)

where $R^1$ to $R^4$ have the abovementioned meanings, and dehydrogenating the tetrahydropyrimidine of the formula IV with Raney nickel at from 150° to 300° C. to give the pyrimidine of the formula I.

12 Claims, No Drawings

PREPARATION OF PYRIMIDINES

The present invention relates to a novel process for preparing 2-substituted pyrimidines by copper(II) acetate-catalyzed reaction of nitriles with 1,3-diaminopropanes to give the 2-substituted 1,4,5,6-tetrahydropyrimidines and subsequent dehydrogenation.

JP 02/104.577 describes a process for preparing tetrahydropyrimidines by reacting nitriles with 1,3-diaminopropanes in the presence of catalysts such as zinc acetate or copper(II) acetate.

Heterocycles 27 (1988) 1867–1871 discloses a two-stage process for preparing 2-alkylpyrimidines, in which, in the first stage, carboxylic acids are reacted with a large excess of 1,3-diaminopropane to give the corresponding 2-alkyl-1,4,5,6-tetrahydropyrimidines and, in the second stage, the purified 2-alkyl-1,4,5,6-tetrahydropyrimidines are dehydrogenated at 320°–350° C. on $Pd/Al_2O_3$ to give the 2-alkylpyrimidine.

The disadvantage of the process is the use of the costly, sensitive palladium catalyst for the dehydrogenation.

It is an object of the present invention to remedy the abovementioned disadvantage.

We have found that this object is achieved by a novel process for preparing pyrimidines of the formula I

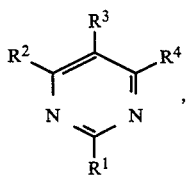
(I)

where
$R^1$ is $C_1$–$C_8$-alkyl, $C_7$–$C_{12}$-aralkyl or phenyl and
$R^2$, $R^3$ and $R^4$ are each, independently of one another, hydrogen, $C_1$–$C_8$-alkyl, $C_7$–$C_{12}$-aralkyl or phenyl,
which comprises reacting nitriles of the formula II

(II)

where $R^1$ has the abovementioned meaning, with 1,3-diaminopropanes of the formula III

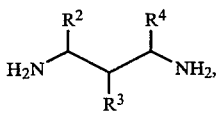
(III)

where $R^2$ to $R^4$ have the abovementioned meanings, in the presence of copper(II) acetate at from 150° to 250C. to give the tetrahydropyrimidine of the formula IV

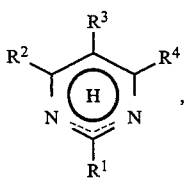
(IV)

where $R^1$ to $R^4$ have the abovementioned meanings, and dehydrogenating the tetrahydropyrimidine of the formula IV with Raney nickel at from 150° to 300° C. to give the pyrimidine of the formula I.

This two-step reaction is preferably carried out as a one-pot synthesis as illustrated by the examples below in which unreacted nitrile II and 1,3-diaminopropane III are removed by distillation from the intermediate tetrahydropyrimidine IV product which is then dehydrogenated in the presence of the Raney nickel catalyst.

The process according to the invention can be carried out by reacting nitriles of the formula II with 1,3-diaminopropanes of the formula III in the stoichiometric amount, or above or below this, preferably in the molar ratio from 0.5:1 to 1.5:1, preferably from 1:1 to 1.1:1, with catalysis by copper(II) acetate to give the 2-substituted 1,4,5,6-tetrahydropyrimidine of the formula IV. The reaction is carried out at from 150° to 250° C., preferably from 180° to 220° C. After the reaction is complete, unreacted nitrile of the formula II and 1,3-diaminopropane of the formula III are removed by distillation, preferably at the reaction temperature and under appropriately reduced pressure. Subsequently, at the reaction temperature, Raney nickel is added, and dehydrogenation is carried out at from 150° to 300° C., preferably from 180° to 250° C., to give the 2-substituted pyrimidine of the formula I. The dehydrogenation is preferably carried out under a pressure at which the 2-substituted pyrimidine of the formula I distils out continuously.

The process according to the invention provides 2-substituted pyrimidines of the formula I in a simpler and more economic way than known processes.

In the compounds I, II, III and IV,
$R^1$, $R^2$, $R^3$ and $R^4$ are each, independently of one another, $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl and isooctyl, preferably $C_1$–$C_4$-alkyl such as methyl, ethyl, n-propyl, isopropyl, n-butyl, isobutyl, sec-butyl and tert-butyl, particularly preferably methyl and ethyl, $C_7$–$C_{12}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, phenyl, $R^2$, $R^3$ and $R^4$ are each hydrogen.

Synthetically prepared pyrimidines are very important intermediates for drugs and for active ingredients in crop protection agents.

EXAMPLES

Example 1

320 g (3.1 mol) of benzonitrile and 5 g of copper(II) acetate are placed in a 1 l stirred flask and, at 180°–190° C., 222 g (3 mol) of 1,3-propylenedianine are added (about 2.5 hours). After a further 3 hours at 180° C., unreacted benzonitrile and 1,3-propylenedianine are distilled out at 180° C./60 mbar, a suspension of 20 g of Raney nickel in 20 ml of dimethylfoznanide is added, and water and dimethylformamide are distilled out at 180° C./60 mbar. The dehydrogenation starts at 245° C.; 2-phenylpyrimidine is distilled out continuously (boiling point 191°–213° C./300 mbar). The yield is 304 g (65%) of a product with a purity of 87%. A further distillation results in 284 g (61%) of 2-phenylpyrimidine with a purity of 99% in the main run at 120°–124° C./4 mbar.

Example 2

363 g (3.1 mol) of phenylacetonitrile and 5 g of copper(II) acetate are placed in a 1 l stirred flask and, at 180°–190° C., 222 g (3 mol) of 1,3-propylenediamine are added (about 2.5 hours). After a further 3 hours at 180° C., unreacted phenylacetonitrile and 1,3-propylenediamine are distilled out at 180° C./60 mbar, a suspension of 20 g of Raney nickel in 20 ml of dimethylformamide is added, and water and dimethylformamide are distilled out at 180° C./60 mbar. The dehydrogenation starts at 245° C.; 2-benzylpyrimidine is distilled out continuously (boiling point 176°–178° C./10 mbar). The yield is 317 g (62%) with a purity of 99%.

We claim:

1. In a two-step process for preparing a substituted pyrimidine of the formula

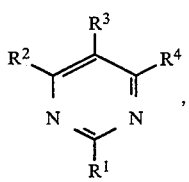

I where
$R^1$ is $C_1$–$C_8$-alkyl, $C_7$–$C_{12}$-aralkyl or phenyl, and
$R^2$, $R^3$ and $R^4$ are each, independently of one another, hydrogen, $C_1$–$C_8$-alkyl, $C_7$–$C_{12}$-aralkyl or phenyl,
by first reacting a nitrile of the formula

II, where
$R^1$ has the abovementioned meaning,
with a 1,3, diaminopropane of the formula

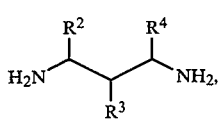

III where
$R^2$ to $R^4$ have the abovementioned meanings,
in the presence of a salt of a metal selected from the group consisting of zinc, copper, iron, cobalt and manganese, at an elevated temperature to produce a tetrahydropyrimidine of the formula

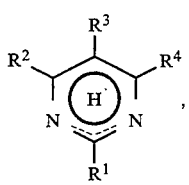

IV where
$R^1$ to $R^4$ have the abovementioned meanings,
and then catalytically dehydrogenating said tetrahydropyrimidine to give said pyrimidine I, the improvement which comprises:

carrying out the dehydrogenation of said tetrahydropyrimidine at a temperature of from 150° to 300° C. in the presence of a Raney nickel catalyst.

2. A process as claimed in claim 1, wherein the pyrimidine IV is distilled out continuously during the dehydrogenation.

3. A process as claimed in claim 1, wherein said nitrile II is reacted with said 1,3-diaminopropane III in the molar ratio from 0.5:1.5 to 1.5:1 at a temperature of 150° to 250° C.

4. A process as claimed in claim 1, wherein said nitrile II is reacted with said 1,3-diaminopropane III in the molar ratio from 1:1 to 1.1:1 at a temperature of 180° to 220° C.

5. A process as claimed in claim 1, wherein the dehydrogenation is carried out at a temperature of from 180° to 250° C.

6. A process as claimed in claim 1, wherein said nitrile II is reacted with said 1,3- diaminopropane III at a temperature of 150° to 250° C. and in the presence of copper (II) acetate as the catalyst.

7. A process as claimed in claim 6, wherein said nitrile II is reacted with said 1,3-diaminopropane III in the molar ratio from 0.5:1.5 to 1.5:1.

8. A one-pot synthesis for preparing a substituted pyrimidine of the formula

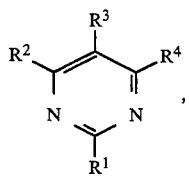

I where
$R^1$ is $C_1$–$C_8$- alkyl, $C_7$–$C_{12}$- aralkyl or phenyl, and
$R^2$, $R^3$ and $R^4$ are each, independently of one another, hydrogen, $C_1$–$C_8$-alkyl, $C_7$–$C_{12}$-aralkyl or phenyl,
which comprises:

(a) first reacting a nitrile of the formula

II, where
$R^1$ has the abovementioned meaning, with a 1,3-diaminopropane of the formula

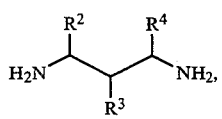

III where
$R^2$ to $R^4$ have the abovementioned meanings,
in the presence of copper(II) acetate at a temperature of 150° to 250° C. to produce a tetrahydropyrimidine of the formula

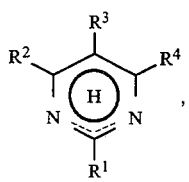

IV where

R$^1$ to R$^4$ have the abovementioned meanings, and, after the reaction is completed, distilling out unreacted nitrile and 1,3- diaminopropane; and (b) thereafter adding a Raney nickel catalyst and catalytically dehydrogenating said tetrahydropyrimidine at a temperature of from 150° to 300° C.

9. A process as claimed in claim 8, wherein the pyrimidine IV is distilled out continuously during the dehydrogenation.

10. A process as claimed in claim 8, wherein said Raney nickel catalyst is added to said tetrahydropyrimidine IV in step (b) in the form of a suspension.

11. A process as claimed in claim 8, wherein said nitrile II is reacted in step (a) with said 1,3-diaminopropane III in the molar ratio from 0.5:1.5 to 1.5:1 at a temperature of 150° to 250°C.

12. A process as claimed in claim 8, wherein said nitrile II is reacted in step (a) with said 1,3-diaminopropane III in the molar ratio from 1:1 to 1.1:1 at a temperature of 180° to 220° C.

* * * * *